United States Patent
Neri et al.

(10) Patent No.: US 6,181,372 B1
(45) Date of Patent: *Jan. 30, 2001

(54) METHOD AND A DEVICE FOR MONITORING THE EXTERNAL INTEGRITY OF CIGARETTES

(75) Inventors: Armando Neri, Bologna; Stefano Chini, San Lazzaro di Savena; Giuseppe Di Stefano, Ferrara, all of (IT)

(73) Assignee: G.D S.p.A., Bologna (IT)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/872,133

(22) Filed: Jun. 10, 1997

(30) Foreign Application Priority Data

Jun. 10, 1996 (IT) .............................................. BO96A0311

(51) Int. Cl.[7] ........................................................ H04N 7/18
(52) U.S. Cl. ............................................. 348/128; 131/280
(58) Field of Search .................................. 348/128, 152, 348/159; 131/280, 281, 21 R; 250/223; 221/135; 73/82, 856; 209/73; 256/237; H04N 7/18

(56) References Cited

U.S. PATENT DOCUMENTS

| | | | |
|---|---|---|---|
| 3,951,267 | * 4/1976 | Reuland | 209/73 |
| 4,121,595 | * 10/1978 | Heitmann et al. | 131/21 R |
| 4,240,448 | * 12/1980 | Heitmann et al. | 131/21 R |
| 4,249,545 | * 2/1981 | Gretz et al. | 131/21 R |
| 4,281,670 | * 8/1981 | Heitmann et al. | 131/281 |
| 4,403,620 | * 9/1983 | Joseph et al. | 131/280 |
| 4,639,592 | * 1/1987 | Heitmann | 250/223 |
| 4,785,830 | * 11/1988 | Moller et al. | 131/84.1 |
| 4,827,947 | * 5/1989 | Hinz | 131/281 |
| 4,906,099 | * 3/1990 | Casassent | 382/143 |
| 5,013,905 | * 5/1991 | Neri | 250/223 |
| 5,287,524 | 2/1994 | Rizzoli et al. | 348/86 |
| 5,347,853 | * 9/1994 | Hoppe et al. | 73/82 |
| 5,432,600 | * 7/1995 | Grollimund et al. | 356/237 |
| 5,560,515 | * 10/1996 | Dyett et al. | 221/135 |
| 5,594,184 | * 1/1997 | Chroder et al. | 73/865 |

FOREIGN PATENT DOCUMENTS

| | | |
|---|---|---|
| 30 30 140 | 3/1982 | (DE) . |
| 3628088 | 2/1988 | (DE) . |
| 548 695 | 6/1993 | (EP) . |
| 570 163 | 11/1993 | (EP) . |
| 2 201 328 | 9/1988 | (GB) . |
| 2 267 474 | 12/1993 | (GB) . |

* cited by examiner

Primary Examiner—Chris S. Kelley
Assistant Examiner—Tung Vo
(74) Attorney, Agent, or Firm—Pillsbury Madison & Sutro LLP

(57) ABSTRACT

The external integrity of cigarettes is verified by a method that involves directing single cigarettes, carried on a conveyor, along a route of which one section affords a monitoring path equipped with a line scan camera; the advancing cigarette can be made selectively to rotate about its longitudinal axis while the camera, a solid state type using CCD arrays, makes a succession of scans on respective closely ordered parallel lines, which are pulsed at a programmed frequency and synchronously with the movement of the cigarette in such a way that each successive scan line will fall on one and the same generator of the cylindrical surface. Repeated scanning of the same limited surface area eliminates quality control errors attributable to the presence of particulates in the space between the cigarettes and the camera.

26 Claims, 2 Drawing Sheets

METHOD AND A DEVICE FOR MONITORING THE EXTERNAL INTEGRITY OF CIGARETTES

BACKGROUND OF THE INVENTION

The present invention relates to a method of verifying the external integrity of cigarettes.

In particular, the invention is pertinent to a method of the aforementioned type such as can be employed, preferably, in cigarette manufacturing machines.

It is standard practice in the art field of cigarette manufacture to verify the external integrity of the finished cigarettes by causing the single cigarettes to advance in succession, with their respective axes disposed transversely to the direction of movement, along a predetermined monitoring path extending past an optical quality control device located following a manufacturing unit in the feed direction.

The quality control device in question is designed to sample a limited number of generators delineating the outer surface of each cigarette produced, by reading images of these same sample generators and comparing each registered image with a model or reference image, to the end of indicating any superficial defects of manufacture that might be present (e.g. badly formed and/or obstructed ventilation holes, edges not gummed, incorrect positioning and/or strength of print, etc.) and thus establishing whether or not the cigarette is of acceptable quality.

The quality control device consists generally in a solid state camera with a CCD array, familiar to those skilled in the art as a Line Scan Camera, which as the name implies is designed to read an object by scanning a single line. In operation, the scan line falls on a sample generator of the outer surface presented by the cigarette passing in front of the camera at a given moment.

It is the usual practice to scan a plurality of sample generators per single cigarette, utilizing a plurality of cameras ranged along the monitoring path: accordingly, the cigarette is made to rotate around its own longitudinal axis while progressing from one camera to the next, so that a different generator will be presented to each camera in turn.

A monitoring method of the type outlined above betrays the drawback that in the event of foreign matter (such as specks of dust, particulates, tobacco filler, etc.) occupying the space in between the cigarette and the optical device during the reading operation, this is interpreted by the device as a flaw and the cigarette will be rejected even though perfectly good. In other words, it cannot be guaranteed a priori that an error signal generated by the device effectively indicates a defective cigarette on every occasion.

The drawback in question is highlighted especially in dusty surroundings, such as those in which a cigarette manufacturing machine will typically operate.

The object of the invention is to provide a method of monitoring the external integrity of cigarettes such as will remain free of the drawback described above.

SUMMARY OF THE INVENTION

The stated object is realized according to the present invention in a method for monitoring the external integrity of cigarettes that comprises the steps of advancing cigarettes in a predetermined feed direction by means of a conveyor, each accommodated within a respective seat afforded by the conveyor and following a path of which one section is a monitoring path, and examining each cigarette in respect of its external characteristics while in movement along the monitoring path.

In the method disclosed, the step of examining the external characteristics of the cigarettes is effected using at least one set of multiline optical scanning means positioned along the monitoring path, such as will execute a plurality of pulsed optical scans at successive intervals. Each scan coincides with one of a cluster of corresponding parallel lines disposed one alongside another, and each cigarette is examined by scanning a given generator of its cylindrical surface more than once on different lines succeeding one another sequentially and synchronously with the movement of the cigarette along the monitoring path in the feed direction.

The stated object is realized similarly, according to the invention, in a device for implementation of the method described above.

A device according to the invention for monitoring the external integrity of cigarettes comprises a conveyor affording a plurality of seats caused to advance in a feed direction along a predetermined path, of which one section is a monitoring path, each accommodating a respective cigarette disposed with its longitudinal axis transverse to the feed direction, and at least one set of optical scanning means located along the monitoring path and designed to examine the external characteristics of at least one generator presented by each cigarette advancing along the monitoring path.

To advantage, the optical scanning means are of a multiline type such as will execute a plurality of discrete scans on a respective plurality of lines disposed parallel with and alongside one another in a cluster; also, the device comprises timing means by which the operation of the optical scanning means is synchronized with the movement of the conveyor so that the plurality of scans will fall on one and the same generator of each advancing cigarette.

In a preferred embodiment, optical scanning means will comprise at least one solid state camera using a CCD array and capable of multiline scanning (referred to conventionally as a Time Delay and Integration Line Scan Camera).

BRIEF DESCRIPTION OF THE DRAWINGS

The invention will now be described in detail, by way of example, with the aid of the accompanying drawings, in which.

DESCRIPTION OF THE PREFERRED EMBODIMENTS

Figure 1:
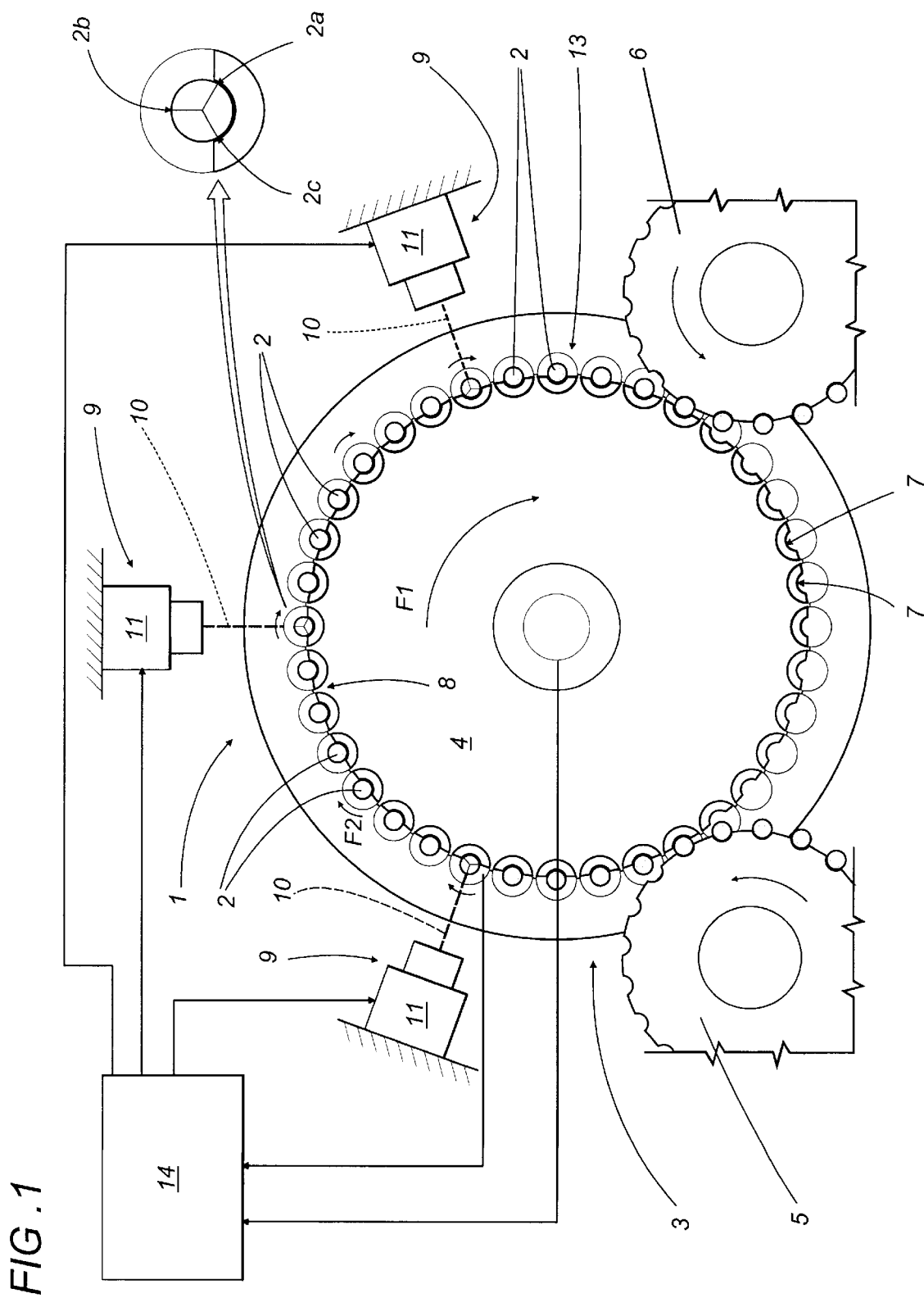
FIG. 1 illustrates a preferred embodiment of the monitoring device according to the present invention, viewed schematically and in elevation.

Referring to the accompanying drawings, 1 denotes a device, in its entirety, for verifying the external integrity of cigarettes 2; such a device comprises a cigarette conveyor 3 equipped with a transfer wheel 4 (conventional in embodiment) forming part of a filter tipping machine. The manufactured cigarettes 2 are fed singly and in succession to the transfer wheel 4 by an infeed wheel 5, then taken up and distanced following verification by an outfeed wheel 6. The various wheels are driven in rotation about their respective axes by means of conventional embodiment not indicated in the drawings.

The transfer wheel 4 incorporates a plurality of peripheral seats 7, each designed to accommodate and to retain a respective cigarette 2, advanced by the wheel 4 in a feed direction denoted F1 (clockwise as viewed in FIG. 1) along a circular path 13 of which one section is a monitoring path 8. Also forming part of the transfer wheel 4 are means not indicated in the drawings, but of conventional design (for example as disclosed in U.S. Pat. No. 5,287,524, to which reference may be made for a fuller description), such as will engage the two longitudinal extremities of each cigarette 2 occupying a respective seat 7 and induce a rotation F2 of the cigarette about its own longitudinal axis. Each cigarette 2 is therefore able to describe a controlled trajectory composed of a translational movement in the feed direction F1 along the monitoring path 8, and a rotation F2 about its own longitudinal axis.

The device 1 comprises means by which to examine the external characteristics presented by at least one generator 2a of each cigarette 2 advancing along the monitoring path 8. Such means consist in optical scanning means 9 of conventional type such as will execute a plurality of optical readings or scans on respective lines 10 extending parallel to the axes of the cigarettes 2.

The single scan lines 10 are disposed parallel with and alongside one another, forming a cluster generated substantially in alignment with the direction along which the cigarettes 2 advance. The optical scans are discrete, pulsed sequentially and at a predetermined frequency to coincide with each line 10 of the cluster from the first through to the last. As the description will show in due course, the optical scanning means 9 are able to examine a given straight line generator 2a of each cigarette 2 several times, the generator for practical purposes being an extremely small portion of the cylindrical surface exhibited by the cigarette 2, appearing substantially rectangular in plan and having a longitudinal dimension equal to the length of the cigarette 2.

The optical scanning means 9 preferably comprise at least one solid state camera 11 incorporating an array of charge-coupled devices (known to persons skilled in the art as a Time Delay & Integration Line Scan Camera) such as will generate a beam comprising a plurality (typically 96) of discrete scans pulsed in succession and coinciding with the respective lines 10 aforementioned. The width of a single scan line 10 is of the order of just a few micrometers, whilst the overall width of the lines generated by the camera 11 in each burst will be greater than the width of the individual line 10 by a factor of at least one or two.

In the solution described and illustrated, use is made of three TDI line scan cameras 11 set apart one from the other along the monitoring path 8, each camera 11 serving to monitor a relative generator 2a, 2b and 2c of the cigarette 2, as will become clear in due course.

The device 1 preferably comprises timing means 14 of conventional embodiment illustrated schematically in FIG. 1, by which the movement of the cigarettes 2 along the monitoring path 8 (that is, to reiterate, translated along the feed direction F1 by the transfer wheel 4 while in rotation F2 about their individual longitudinal axes) can be synchronized with the scanning frequency of the cameras 11 in such a way that the cluster of lines 10 scanned in a typical burst by any one camera 11 will always fall substantially on the same generator 2a of the cigarette 2 advancing at a given moment past that camera 11. Thus, the timing means 14 control both the transfer wheel 4 and the means by which the individual cigarettes 2 are made to rotate about their own axis.

When, during operation of the device, a given generator 2a of an advancing cigarette 2 is rotated exactly into alignment with the first of the cluster of lines 10 relative to the first camera 11, this same camera will begin scanning. With the cigarette 2 then continuing to advance and to rotate (in the direction denoted F2) the same generator 2a (i.e. that already scanned on the first line) will be brought exactly into alignment with the second line 10 of the cluster, whereupon the first camera 11 makes a second scan; and so on for the remaining lines 10 of the cluster.

Figure 2:
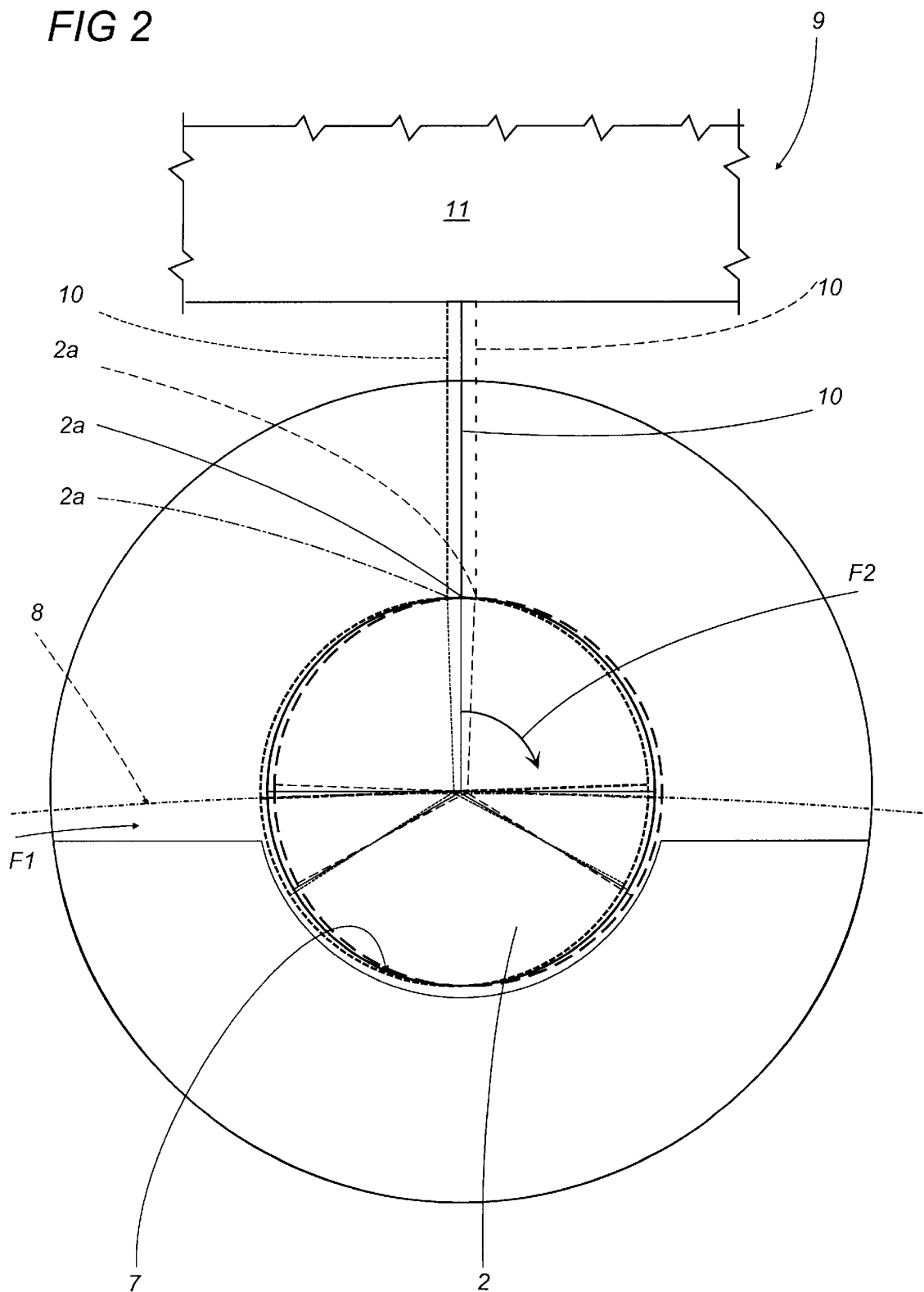
FIG. 2 illustrates a detail of the device of FIG. 1, shown enlarged and in successive steps of operation.

Given that the lines 10 of the cluster are scanned typically at a rate (expressible mathematically as the distance between any two adjacent lines 10 multiplied by the frequency of the scan pulses) faster than the velocity at which the cigarettes 2 advance along the monitoring path 8 in the feed direction F1, it follows that if a cigarette 2 were not rotated about its own axis, there would be a built-in delay relative to the scan pulses and each successive scan would therefore fall on a different generator. Precisely in order to avoid such a situation, the cigarette 2 is made to rotate about its own axis in the same direction of rotation as that described by the transfer wheel 4 (see FIG. 2), so that the single generator being scanned can keep pace positionally with the pulses. FIG. 2 shows the positions assumed successively by the cigarette 2 in relation to three different scan lines 10 during the burst generated by a given camera 11.

Each image scanned is compared by the device 1 with a reference image in the usual manner. In the event of the space between a given camera 11 and a cigarette 2 being invaded by one or more foreign bodies (specks of dust, particles of tobacco filler, etc.), then certain of the scans made by that camera could produce images dissimilar to the reference image, due to the presence of such matter (and not by reason of any real defect in the cigarette 2). This need not necessarily result in the rejection of the cigarette 2, however, given that the majority of the scans will not be affected by the presence of particulates: indeed the typical size of a particle liable to be detected is much less than the overall width of the cluster of lines 10 scanned by a camera 11 in one burst.

The requisite number of scans being completed, the device 1 proceeds to determine the ratio between those resulting "positive", i.e. reflecting an irregularity in the cigarette 2, and those which are "negative"; in the event of the ratio exceeding a preset value (reprogrammable), the device 1 responds in conventional manner by generating an output signal that might be utilized, for example, to pilot the operation of a reject device (not illustrated) located further along the manufacturing line.

Once beyond the first camera, and before reaching the second camera, the single cigarette 2 can be rotated about its axis (for example through 120°) in such a way that the second camera scans a different generator of the cigarette 2, denoted 2b in FIG. 1, whereupon the cycle of operations described above is repeated.

Thereafter, these same operations are again repeated by the third camera on a third generator, denoted 2c in the example illustrated.

Clearly it would be possible to use a greater number of cameras 11 installed along the monitoring path 8, so that different generators of each cigarette 2 can be examined, though still with each camera scanning a single generator several times.

The facility of causing a cigarette 2 to rotate in the direction denoted F2 about its own axis serves a dual function: first, the motion of the cigarette 2 can be synchronized with the operation of a camera 11 that is set up to scan a plurality of lines 10, so that a given generator can be examined repeatedly by the one camera with no need to adopt an excessive peripheral velocity of the transfer wheel 4; second, it becomes possible to sample several generators of the same cigarette 2.

Finally, and with a high level of dependability in quality control still as the aim, the sampling of single generators by repeated scanning (as defined in the foregoing description) can be extended in accordance with the present invention to compass any given number of generators, and therefore a portion of any width presented by the cylindrical surface of the single cigarette.

What is claimed is:

1. A method for monitoring the external integrity of cigarettes, comprising the steps of:

advancing single cigarettes in a predetermined feed direction by means of a conveyor, each accommodated within a relative seat afforded by the conveyor and made to follow a path of which one section is a monitoring path;

examining external characteristics of the cigarettes while in movement along the monitoring path using at least one set of multiline optical scanning means positioned along the monitoring path, such as will execute a plurality of pulsed optical scans at successive intervals;

performing each pulsed scan on a same single given generator line of the cylindrical surface of the cigarette, during the movement of the cigarette along the monitoring path, so determining a surface swept by the given generator line, the surface being formed by a cluster of parallel lines disposed one alongside another;

performing each pulsed scan by the at least one multiline optical scanner more than once, sequentially and synchronously with the movement of the same single given generator line of the cylindrical surface of the cigarette along the monitoring path in the feed direction;

comparing each scanned image of each generator line with a reference image, assigning to the image a positive mark if the scanned image is dissimilar to the reference image, and assigning a negative mark to the image if the scanned image is in accordance with the reference image;

determining a ratio between the positive marks and the negative marks of the scanned images, in the event of the ratio exceeds a reprogrammable preset value, generating an output signal; and rejecting the corresponding cigarette if the output signal is generated.

2. A method as in claim 1, comprising the further steps of enforcing a rotation of each cigarette about its own longitudinal axis in a given direction at least when crossing the scan lines, and of synchronizing the scan lines with the movements of the cigarette along the feed direction and in rotation about its own axis in such a way that the same generator is scanned repeatedly.

3. A method as in claim 1, comprising the further steps of enforcing a rotation of each cigarette about its own longitudinal axis in a given direction at least when crossing the scan lines, and of synchronizing the scan lines with the movements of the cigarette along the feed direction and in rotation about its own axis in such a way that the same generator is scanned repeatedly, wherein the optical scanning means comprise at least one solid state camera capable of multiline scanning.

4. A method as in claim 2, wherein use is made of a plurality of optical scanning means distributed along the monitoring path, comprising the further step of causing the cigarette to rotate about its own longitudinal axis when advancing between one set of optical scanning means and the next in order to allow the examination of more than one generator presented by each cigarette.

5. A device for monitoring the external integrity of cigarettes, comprising:

a conveyor affording a plurality of seats caused to advance in a feed direction along a predetermined path of which one section is a monitoring path, each accommodating a relative cigarette disposed with its longitudinal axis transverse to the feed direction;

at least one set of optical scanning means positioned along the monitoring path and designed to examine the external characteristics of at least one generator presented by each cigarette advancing along the monitoring path, wherein the optical scanning means are of a type such as will execute a plurality of discrete scans on a respective plurality of lines disposed parallel with and alongside one another in a cluster;

timing means by which the operation of the optical scanning means is synchronized with the movement of the conveyor in such a way that the plurality of scans will fall on one and the same generator of each advancing cigarette;

a comparing device in which each scanned image of each generator line is compared with a reference image, assigning a positive mark if the scanned image is dissimilar to the reference image, and assigning a negative mark if the scanned image is in accordance with the reference image;

an output device determining a ratio between the positive marks and the negative marks of the scanned images, and generating an output signal, in the event of the ratio exceeds a reprogrammable preset value; and a device for rejecting the corresponding cigarette if the output signal is generated.

6. A device as in claim 5, wherein the conveyor comprises a transfer wheel rotatable about its own axis, of which the periphery affords a plurality of seats accommodating the cigarettes, and means operating synchronously with the optical scanning means, by which each cigarette occupying a respective seat is caused to rotate about its own longitudinal axis when crossing the scan lines.

7. A device as in claim 5, wherein the conveyor comprises a transfer wheel rotatable about its own axis, of which the periphery affords a plurality of seats accommodating the cigarettes, and means operating synchronously with the optical scanning means, by which each cigarette occupying a respective seat is caused to rotate about its own longitudinal axis when crossing the scan lines, the optical scanning means comprising at least one solid state camera capable of multiline scanning.

8. A device as in claim 5, comprising a plurality of optical scanning means distributed along the monitoring path, serving in operation respectively to examine a single generator of each advancing cigarette, also means of conventional embodiment by which each cigarette occupying a respective seat is caused to rotate about its own longitudinal axis when advancing between one set of optical scanning means and the next.

9. A method for monitoring the external integrity of cigarettes, comprising the steps of:

advancing single cigarettes in a predetermined feed direction by a conveyor, each accommodated within a relative sea afforded by the conveyor and made to follow a path of which one section is a monitoring path;

examining external characteristics of the cigarettes while in movement along the monitoring path using at least one multiline optical scanner positioned along the monitoring path, such as will execute a plurality of pulsed optical scans at successive intervals;

performing each pulsed scan on a same single given generator line of the cylindrical surface of the cigarette, during the movement of the cigarette along the monitoring path, so determining a surface swept by the give generator line, the surface being formed by a cluster of parallel lines disposed one alongside another;

performing each pulsed scan by the at least one multiline optical scanner more than once, sequentially and synchronously with the movement of the movement of the same single given generator line of the cylindrical surface of the cigarette along the monitoring path in the feed direction;

comparing each scanned image of each generator line with a reference image, assigning to the image a positive mark if the scanned image is dissimilar to the reference image, and assigning a negative mark to the image if the scanned image is in accordance with the reference image;

determining a ratio between the positive marks and the negative marks of the scanned images, in the event of the ratio exceeds a reprogrammable preset value, generating an output signal; and rejecting the corresponding cigarette if the output signal is generated.

10. A method as in claim 9, comprising the further steps of enforcing a rotation of each cigarette about its own longitudinal axis in a given direction at least when crossing the scan lines, and of synchronizing the scan lines with the movements of the cigarette along the feed direction and in rotation about its own axis in such a way that the same generator is scanned repeatedly.

11. A method as in claim 9, comprising the further steps of enforcing a rotation of each cigarette about its own longitudinal axis in a given direction at least when crossing the scan lines, and of synchronizing the scan lines with the movements of the cigarette along the feed direction and in rotation about its own axis in such a way that the same generator is scanned repeatedly, wherein the optical scanner comprises at least one solid state camera capable of multiline scanning.

12. A method as in claim 10, wherein use is made of a plurality of optical scanners distributed along the monitoring path, comprising the further step of causing the cigarette to rotate about its own longitudinal axis when advancing between one optical scanner and the next in order to allow the examination of more than one generator presented by each cigarette.

13. A device for monitoring the external integrity of cigarettes, comprising:

a conveyor affording a plurality of seats caused to advance in a feed direction along a predetermined path of which one section is a monitoring path, each accommodating a relative cigarette disposed with its longitudinal axis transverse to the feed direction;

at least one optical scanner positioned along the monitoring path and designed to examine the external characteristics of at least one generator presented by each cigarette advancing along the monitoring path, wherein the optical scanner is of a type such as will execute a plurality of discrete scan on a respective plurality lines disposed parallel with and alongside one another in a cluster;

a timing mechanism to synchronize the operation of the optical scanner with the movement of the conveyor in such a way that a plurality of scans will fall on one and the same generator of each advancing cigarette;

a comparing device in which each scanned image of each generator line is compared with a reference image, assigning a positive mark if the scanned image is dissimilar to the reference image, and assigning a negative mark if the scanned image is in accordance with the reference image;

an output device determining a ratio between the positive marks and the negative marks of the scanned images, and generating an output signal, in the event of the ratio exceeds a reprogrammable preset value; and a device for rejecting the corresponding cigarette if the output signal is generated.

14. A device as in claim 13, wherein the conveyor comprises a transfer wheel rotatable about its own axis, of which the periphery affords a plurality of seats accommodating the cigarettes, and a rotating mechanism operating synchronously with the optical scanner, by which each cigarette occupying a respective seat is caused to rotate about its own longitudinal axis when crossing the scan lines.

15. A device as in claim 13, wherein the conveyor comprises a transfer wheel rotatable about its own axis, of which the periphery affords a plurality of seats accommodating the cigarettes, and a rotating mechanism operating synchronously with the optical scanner, by which each cigarette occupying a respective seat is caused to rotate about its own longitudinal axis when crossing the scan lines, the optical scanner comprising at least one solid state camera capable of multiline scanning.

16. A device as in claim 13, comprising a plurality of optical scanners distributed along the monitoring path, serving in operation respectively to examine a single generator of each advancing cigarette, and a rotating mechanism by which each cigarette occupying a respective seat is caused to rotate about its own longitudinal axis when advancing between one optical scanner and the next.

17. A method of monitoring the external integrity of cylindrical objects, comprising the steps of:

advancing single cylindrical object along a monitoring path at a determined rate by a conveyor, each cylindrical object accommodated within a relative seat of the conveyor;

examining external characteristics of at least one of the cylindrical objects using at least one multiline scanner positioned along the monitoring path, the scanner adapted to execute a plurality of pulsed scans at successive time intervals, each of the pulsed scans parallel to one another and spaced apart from each other by a determined distance;

performing a plurality of pulsed scan on the cylindrical object, object, whereby the time and distance spacing of the plurality of pulsed scans is set to correspond to the rate of movement of the cylindrical object along the monitoring path such that each of the plurality of pulsed scans falls on a same single given generator line of an external surface of the cylindrical object.

18. A method as in claim 17 and comprising the further steps of:

comparing each scanned image of the single given generator line with a reference image, assigning to the image a first mark if the scanned image is dissimilar to the reference image, and assigning a second mark to the image if the scanned image is in accordance with the reference image;

determining a ratio between a sum of the first marks and a sum of the second marks and rejecting the cylindrical object if the ratio exceeds a predetermined value.

19. A method as claim 18, comprising the further steps of:
rotating the cylindrical object cigarette at a predetermined rate about its own longitudinal axis in a given direction along a portion of the monitoring path, and
synchronizing the rate of rotation of the cylindrical object with the rate of movement along the monitoring path such that each of the plurality of pulsed scans falls on the same single given generator line of the cylindrical object.

20. A method as in claim 19, wherein use is made of a plurality of optical scanners distributed along the monitoring path, wherein the cylindrical object rotates when advancing between one optical scanner and the next in order to allow the examination of more than one line generator of the cylindrical.

21. A method as claim 20, wherein the optical scanner comprises at least one solid state camera capable of multi-line scanning.

22. A device for monitoring the external integrity of cylindrical objects, comprising:
a conveyor adapted to advance at a predetermined rate in a feed direction along a predetermined monitoring path, the conveyor including a plurality of seats each adapted to accommodate a relative cylindrical object disposed with its longitudinal axis transverse to the feed direction;
at least one scanner positioned along the monitoring path adapted to examine external characteristics of at least one line generator of an external surface of a cylindrical object advanced along the monitoring path, wherein the scanner is adapted to execute a plurality of pulsed scans at successive time intervals, each of the pulsed scans parallel to one another and spaced apart from each other by a determined distance;
a timing mechanism to synchronize the operation of the optical scanner with the movement of the conveyor in such a way that the plurality of scans will fall on a same single line generator of the advancing cylindrical object.

23. A device as in claim 22 and further comprising,
a comparing device in which each scanned image of each generator line is compared with a reference image, the comparing device assigning a first mark if the scanned image is dissimilar to the reference image, and assigning a second mark if the scanned image is in accordance with the reference image;
an output device determining a ratio between a sum of the first marks and a sum of the second marks and generating an output signal if the ratio exceeds a preset value; and
a rejection device for rejecting the corresponding cylindrical object if the output signal is generated.

24. A device as in claim 23, wherein the conveyor comprises a transfer wheel rotatable about its own axis, and having at a periphery thereof a plurality of seats adapted to accommodate the cylindrical object, and a seat rotating mechanism for rotating each of the cylindrical objects at a predetermined rate about its own longitudinal axis operating synchronously with the rate of movement along the monitoring path such that each of the plurality of pulsed scans falls on the same single given line generator of the cylindrical object.

25. A device as in claim 24, and further comprising a plurality of optical scanners distributed along the monitoring path, each adapted respectively to examine a different single line generator of each advancing cylindrical object, whereby each cylindrical object is rotated by the seat rotating mechanism when advancing between one optical scanner and the next.

26. A device as in claim 25, the optical scanner comprising at least one solid state camera capable of multiline scanning.

* * * * *